United States Patent
Agrawal et al.

(10) Patent No.: US 7,671,035 B2
(45) Date of Patent: Mar. 2, 2010

(54) EPIDERMAL GROWTH FACTOR RECEPTOR ANTISENSE OLIGONUCLEOTIDES

(75) Inventors: Sudhir Agrawal, Shrewsbury, MA (US); Ekambar R. Kandimalla, Southboro, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 1237 days.

(21) Appl. No.: 10/140,228

(22) Filed: May 7, 2002

(65) Prior Publication Data
US 2003/0045494 A1 Mar. 6, 2003

Related U.S. Application Data

(60) Provisional application No. 60/289,055, filed on May 7, 2001, provisional application No. 60/289,149, filed on May 7, 2001.

(51) Int. Cl.
*A01N 43/04* (2006.01)
*A61K 31/70* (2006.01)
(52) U.S. Cl. ........................................ 514/44
(58) Field of Classification Search ................. 536/24.5, 536/23.1; 514/44; 435/6, 325, 375
See application file for complete search history.

(56) References Cited

U.S. PATENT DOCUMENTS

| 5,627,053 A | * | 5/1997 | Usman et al. | ............. | 435/91.1 |
| 5,824,475 A | * | 10/1998 | Nelson et al. | ............. | 435/6 |
| 6,083,695 A | * | 7/2000 | Hardin et al. | ............. | 435/6 |
| 6,277,640 B1 | * | 8/2001 | Bennett et al. | ............. | 435/455 |
| 6,582,908 B2 | * | 6/2003 | Fodor et al. | ............. | 506/9 |
| 6,821,724 B1 | * | 11/2004 | Mittman et al. | ............. | 435/6 |
| 7,205,146 B1 | * | 4/2007 | Keith et al. | ............. | 435/325 |

OTHER PUBLICATIONS

Revision history of GenBank No. M34309 (http://www.ncbi.nlm.nih.gov/entrez/sutils/girevhist.cgi?val=M34309) retrieved from NCBI on Jan. 9, 2008.*
Buck et al (Biotechniques (1999) 27(3):528-536).*
GenBank [online] Bethesda, MD USA: United States National Library of Medicine [retrieved on Feb. 3, 2009]. Retrieved from:GenBank accession No. M34309.*
Salomon et al. (Crit. Rev. Oncol. Hematol 19:183-232, 1995).*

* cited by examiner

*Primary Examiner*—Brian Whiteman
(74) *Attorney, Agent, or Firm*—Keown & Zucchero, LLP; Wayne A. Keown; Joseph C. Zucchero

(57) ABSTRACT

Disclosed are synthetic oligonucleotides complementary to nucleic acids encoding epidermal growth factor and methods of their use.

13 Claims, 6 Drawing Sheets

1    2    3    4    5
FIG. 3A
             p27— 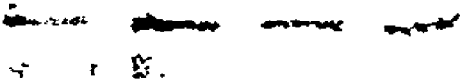
FIG. 3B   p27— 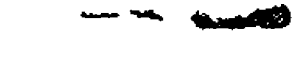

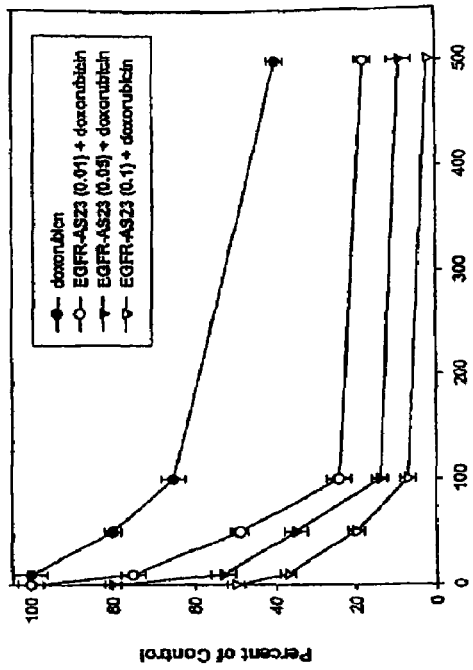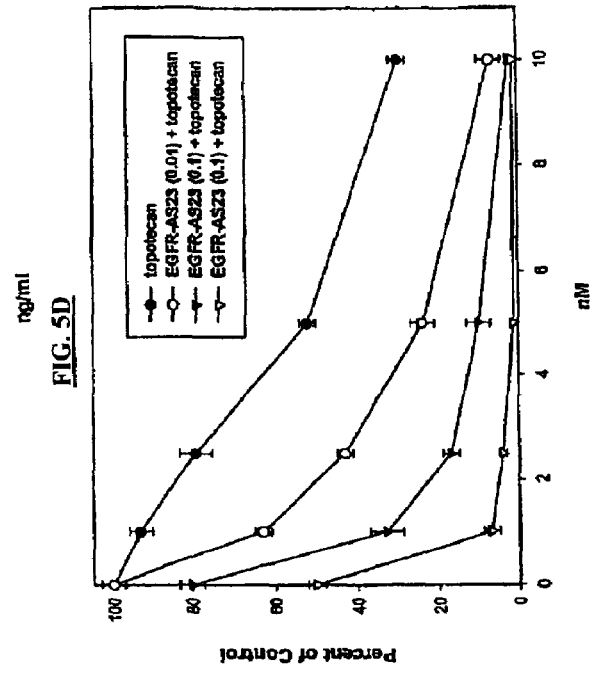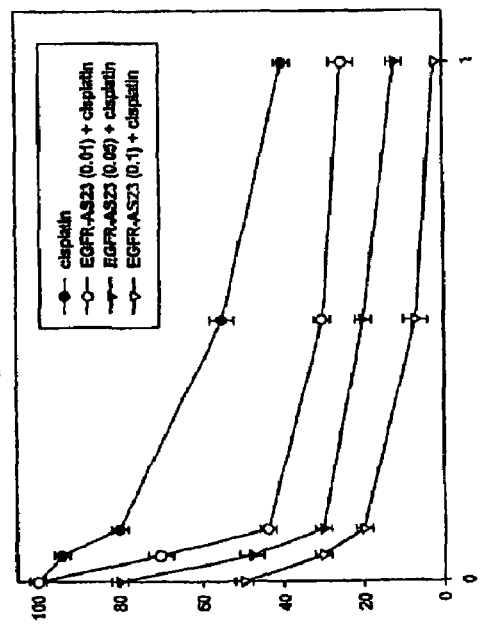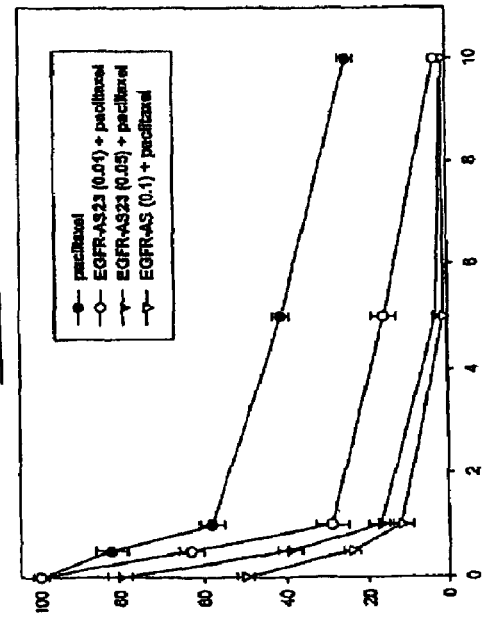

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
acactgcctg agagttgccc                                               20

<210> SEQ ID NO 2
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 2
ccatcaccac ctcacacctc                                               20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
ggtcttggtc aatgtctggc                                               20

<210> SEQ ID NO 4
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 4
tctacttcca tcttgtcagg                                               20

<210> SEQ ID NO 5
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 5
gtccactctt gtcctcaatg                                               20

<210> SEQ ID NO 6
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 6
tccaacactt gaccatcacc                                               20

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
ctggctccag ctctacttcc                                               20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
tggactgtgc cttctcctcc                                               20
```

<210> SEQ ID NO 9
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 9
gctctcatct cttcataccc                                              20

<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
ctcttcttga cagtctgatg                                              20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
actttaatgc agactggaat                                              20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
gtcctcaatg actttaatgc                                              20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
agcttgaaaa ctctgccgtc                                              20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
tatgatctgt cacagcttga                                              20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 15
ttgctcagat gctgggcagg                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
cttcataccc ttgctacgat                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
cccctgaaaa gctctcatct                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cctgatgtcc aggcccctga                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
ggaaacaaag gcacacataa                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cagtctgatg ggaaacaaag                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21 cctcccttc ctcttcttga                                               20

<210> SEQ ID NO 22
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
tgctaggttt cctcccttc                                                  20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
uaugatctgt cacagcuuga                                                 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ugctaggttt cctcccuuuc                                                 20

<210> SEQ ID NO 25
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 25
actcctccat actga                                                      15

<210> SEQ ID NO 26
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 26
acaagtatca gagcc                                                      15

<210> SEQ ID NO 27
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 27
gtggtggtag cagagctgcc tattg                                           25

<210> SEQ ID NO 28
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 28
```

-continued

```
tgacacagga tgtttgatcc accac                                         25

<210> SEQ ID NO 29
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 29
ucgcacccat ctctctccuu c                                             21

<210> SEQ ID NO 30
<211> LENGTH: 4975
<212> TYPE: DNA
<213> ORGANISM: Artificial Sequence
<220> FEATURE:
<223> OTHER INFORMATION: Antisense Oligonucleotide

<400> SEQUENCE: 30
ctctcacaca cacacacccc tcccctgcca tccctcccccg gactccggct ccggctccga   60
ttgcaatttg caacctccgc tgccgtcgcc gcagcagcca ccaattcgcc agcggttcag   120
gtggctcttg cctcgatgtc ctagcctagg ggccccgggg ccggacttgg ctgggctccc   180
ttcaccctct gcggagtcat gagggcgaac gacgctctgc aggtgctggg cttgcttttc   240
agcctggccc ggggctccga ggtgggcaac tctcaggcag tgtgtcctgg gactctgaat   300
ggcctgagtg tgaccggcga tgctgagaac caataccaga cactgtacaa gctctacgag   360
aggtgtgagg tggtgatggg gaaccttgag attgtgctca cgggacacaa tgccgacctc   420
tccttcctgc agtggattcg agaagtgaca ggctatgtcc tcgtggccat gaatgaattc   480
tctactctac cattgcccaa cctccgcgtg gtgcgaggga cccaggtcta cgatgggaag   540
tttgccatct tcgtcatgtt gaactataac accaactcca gccacgctct cgccagctc   600 cgcttgactc agctcaccga gattctgtca gggggtgttt atattgagaa gaacgataag   660 cttttgtcaca tggacacaat tgactggagg gacatcgtga gggaccgaga tgctgagata   720
gtggtgaagg acaatggcag aagctgtccc ccctgtcatg aggtttgcaa ggggcgatgc   780 tgggggtcctg gatcagaaga ctgccagaca ttgaccaaga ccatctgtgc tcctcagtgt   840
aatggtcact gctttgggcc caaccccaac cagtgctgcc atgatgagtg tgccggggggc   900 tgctcaggcc ctcaggacac agactgcttt gcctgccgcc acttcaatga cagtggagcc   960
tgtgtacctc gctgtccaca gcctcttgtc tacaacaagc taactttcca gctggaaccc   1020 aatcccccaca ccaagtatca gtatggagga gtttgtgtag ccagctgtcc ccataacttt   1080
gtggtggatc aaacatcctg tgtcagggcc tgtcctcctg acaagatgga agtagataaa   1140
aatgggctca gatgtgtgga ccttgtgggg gactatgtc ccaaagcctg tgagggaaca   1200
ggctctggga gccgcttcca gactgtggac tcgagcaaca ttgatggatt tgtgaactgc   1260
accaagatcc tgggcaacct ggactttctg atcaccggcc tcaatggaga ccctggcac   1320 aagatccctg ccctggaccc agagaagctc aatgtcttcc ggacagtacg ggagatcaca   1380
ggttacctga acatccagtc ctggccgccc cacatgcaca acttcagtgt tttttccaat   1440
ttgacaacca ttggaggcag aagcctctac aaccggggct tctcattgtt gatcatgaag   1500
aacttgaatg tcacatctct gggcttccga tccctgaagg aaattagtgc tgggcgtatc   1560
tatataagtg ccaataggca gctctgctac caccactctt tgaactggac caaggtgctt   1620
```

```
cgggggccta cggaagagcg actagacatc aagcataatc ggccgcgcag agactgcgtg      1680
gcagagggca aagtgtgtga cccactgtgc tcctctgggg gatgctgggg cccaggccct      1740
ggtcagtgct tgtcctgtcg aaattatagc cgaggaggtg tctgtgtgac ccactgcaac      1800
tttctgaatg gggagcctcg agaatttgcc catgaggccg aatgcttctc ctgccacccg      1860
gaatgccaac ccatgggggg cactgccaca tgcaatggct cgggctctga tacttgtgct      1920
caatgtgccc attttcgaga tgggcccccac tgtgtgagca gctgccccca tggagtccta     1980
ggtgccaagg gcccaatcta caagtaccca gatgttcaga atgaatgtcg gccctgccat      2040
gagaactgca cccaggggtg taaaggacca gagcttcaag actgtttagg acaaacactg      2100
gtgctgatcg gcaaaaccca tctgacaatg gctttgacag tgatagcagg attggtagtg      2160
attttcatga tgctgggcgg cacttttctc tactggcgtg ggcgccggat tcagaataaa      2220
agggctatga ggcgatactt ggaacggggt gagagcatag agcctctgga ccccagtgag      2280
aaggctaaca aagtcttggc cagaatcttc aaagagacag agctaaggaa gcttaaagtg      2340
cttggctcgg gtgtctttgg aactgtgcac aaaggagtgt ggatccctga gggtgaatca      2400
atcaagattc cagtctgcat taaagtcatt gaggacaaga gtggacggca gagttttcaa      2460
gctgtgacag atcatatgct ggccattggc agcctggacc atgcccacat tgtaaggctg      2520
ctgggactat gcccagggtc atctctgcag cttgtcactc aatatttgcc tctgggttct      2580
ctgctggatc atgtgagaca acaccggggg gcactggggc acagctgct gctcaactgg       2640 ggagtacaaa ttgccaaggg aatgtactac cttgaggaac atggtatggt gcatagaaac      2700
ctggctgccc gaaacgtgct actcaagtca cccagtcagg ttcaggtggc agattttggt      2760
gtggctgacc tgctgcctcc tgatgataag cagctgctat acagtgaggc caagactcca      2820
attaagtgga tggcccttga gagtatccac tttgggaaat acacacacca gagtgatgtc      2880
tggagctatg gtgtgacagt ttgggagttg atgaccttcg gggcagagcc ctatgcaggg      2940
ctacgattgg ctgaagtacc agacctgcta gagaagggggg agcggttggc acagccccag     3000
atctgcacaa ttgatgtcta catggtgatg gtcaagtgtt ggatgattga tgagaacatt      3060
cgcccaacct ttaaagaact agccaatgag ttcaccagga tggcccgaga cccaccacgg      3120
tatctggtca taaagagaga gagtgggcct ggaatagccc ctgggccaga gccccatggt      3180
ctgacaaaca agaagctaga ggaagtagag ctggagccag aactagacct agacctagac      3240
ttggaagcag aggaggacaa cctggcaacc accacactgg gctccgccct cagcctacca      3300
gttggaacac ttaatcggcc acgtgggagc cagagccttt taagtccatc atctggatac      3360
atgcccatga accagggtaa tcttgggggg tcttgccagg agtctgcagt ttctgggagc      3420
agtgaacggt gcccccgtcc agtctctcta cacccaatgc cacggggatg cctggcatca      3480
gagtcatcag aggggcatgt aacaggctct gaggctgagc tccaggagaa agtgtcaatg      3540
tgtagaagcc ggagcaggag ccggagccca cggccacgcg gagatagcgc ctaccattcc      3600
cagcgccaca gtctgctgac tcctgttacc ccactctccc cacccgggtt agaggaagag      3660
gatgtcaacg gttatgtcat gccagataca cacctcaaag gtactccctc ctcccgggaa      3720 ggcaccctt cttcagtggg tctcagttct gtcctgggta ctgaagaaga agatgaagat       3780
gaggagtatg aatacatgaa ccggaggaga aggcacagtc cacctcatcc ccctaggcca      3840
agttcccttg aggagctggg ttatgagtac atggatgtgg ggtcagacct cagtgcctct      3900
ctgggcagca cacagagttg cccactccac cctgtaccca tcatgcccac tgcaggcaca      3960
actccagatg aagactatga atatatgaat cggcaacgag atgaggtgg tcctgggggt      4020
```

```
gattatgcag ccatgggggc ctgcccagca tctgagcaag ggtatgaaga gatgagagct    4080
tttcaggggc ctggacatca ggcccccat  gtccattatg cccgcctaaa aactctacgt    4140
agcttagagg ctacagactc tgcctttgat aaccctgatt actggcatag caggcttttc    4200
cccaaggcta atgcccagag aacgtaactc ctgctccctg tggcactcag ggagcattta    4260
atggcagcta gtgcctttag agggtaccgt cttctcccta ttccctctct ctcccaggtc    4320
ccagcccctt ttccccagtc ccagacaatt ccattcaatc tttggaggct tttaaacatt    4380
ttgacacaaa attcttatgg tatgtagcca gctgtgcact ttcttctctt tcccaacccc    4440
aggaaaggtt ttccttattt tgtgtgcttt cccagtccca ttcctcagct tcttcacagg    4500
cactcctgga gatatgaagg attactctcc atatcccttc ctctcaggct cttgactact    4560
tggaactagg ctcttatgtg tgcctttgtt tcccatcaga ctgtcaagaa gaggaaaggg    4620
aggaaaccta gcagaggaaa gtgtaatttt ggtttatgac tcttaacccc ctagaaagac    4680
agaagcttaa aatctgtgaa gaaagaggtt aggagtagat attgattact atcataattc    4740
agcacttaac tatgagccag gcatcatact aaacttcacc tacattatct cacttagtcc    4800
tttatcatcc ttaaaacaat tctgtgacat acatattatc tcattttaca caaagggaag    4860
tcgggcatgg tggctcatgc ctgtaatctc agcactttgg gaggctgagg cagaaggatt    4920
acctgaggca aggagtttga gaccagctta gccaacatag taagacccc  atctc         4975
```

EPIDERMAL GROWTH FACTOR RECEPTOR ANTISENSE OLIGONUCLEOTIDES

CROSS-REFERENCE TO RELATED APPLICATIONS

This application claims priority to U.S. Provisional Application Ser. No. 60/289,055, filed May 7, 2001, and U.S. Provisional Application Ser. No. 60/289,149, filed May 7, 2001, which are incorporated herein by reference in their entirety.

BACKGROUND OF THE INVENTION

1. Field of the Invention

This invention relates to the fields of cell biology, medicine and cancer. More specifically, this invention is related to the control of cell proliferation through antisense technology.

2. Description of the Related Art

Peptide growth factors are key regulators of normal and cancer cell proliferation and differentiation (Salomon et al. (1995) *Crit. Rev. Oncol. Hematol.* 19:183-232). Growth factors of the epidermal growth factor (EGF) gene family, such as transforming growth factor α (TGFα), act as autocrine and paracrine mitogens for human epithelial cancers including breast, colon, ovary, kidney, prostate and lung (Salomon et al. (1995) *Crit. Rev. Oncol. Hematol.* 19:183-232). TGFα binds to the extracellular domain of the epidermal growth factor receptor (EGFR) and activates its intracellular tyrosine kinase domain (Salomon et al. (1995) *Crit. Rev. Oncol. Hematol.* 19:183-232). Enhanced expression of TGFα and/or EGFR has been detected in the majority of human carcinomas and is associated with poor prognosis (Salomon et al. (1995) *Crit. Rev. Oncol. Hematol* 19:183-232). Therefore, the TGFα-EGFR autocrine pathway has been proposed as a therapeutic target (Mendelsohn (1997) *J. Natl. Cancer Inst.* 89:341-343; Mendelsohn (1997) *Clin. Cancer Res.* 3:2703-2707).

Different pharmacologic and biologic approaches have been developed for blocking EGFR activation and/or function in cancer cells. For example, various anti-EGFR blocking monoclonal antibodies (MAb), recombinant proteins containing TGFα or EGF fused to toxins, and EGFR tyrosine kinase inhibitors have been generated and characterized for their biologic and potentially therapeutic properties (Fan et al. (1998) *Curr. Opin. Oncol.* 10:67-73). MAb C225, a chimeric human-mouse IgG$_1$ MAb, is in phases II-III clinical trials in cancer patients (Fan et al., supra). Compounds that selectively block the ligand-induced activation of the EGFR tyrosine kinase (EGFR tyrosine kinase inhibitors, such as ZD1839) (Ciardiello et al., (2000) *Clin. Cancer Res.* 6(5):2053-2063 are also currently under clinical evaluation in cancer patients (Noonberg (2000) *Drugs* 59:753-67). Previous studies have demonstrated that agents such as MAb C225 interfere with EGFR activation, potentiate the antitumor activity of cytotoxic drugs, including platinum-derivatives, taxanes, topoisomerase I and II inhibitors (Mendelsohn (1997) *J. Natl. Cancer Inst.* 89:341-343; Mendelsohn (1997) *Clin. Cancer Res.* 3:2703-2707; Ciardiello et al. (1999) *Clin. Cancer Res.* 5:909-916) or EGFR tyrosine kinase inhibitors (Ciardiello et al. (2000) supra).

Unfortunately, none of these approaches have yet emerged as an effective therapeutic. There is, therefore, a need for new approaches to blocking EGFR activity in cancer cells.

SUMMARY OF THE INVENTION

The present invention provides new methods for blocking EGFR activity in cancer cells.

It has been discovered that oligonucleotides directed to EGFR-specific mRNA reduces EGFR expression and inhibits cancer cell growth in vitro. In addition, it has also been determined that oligonucleotides modified as hybrid DNA/RNA mixed backbone oligonucleotides (MBOs) specifically target EGFR mRNA sequences and block EGFR synthesis, inhibit cell growth, and enhance apoptosis, or programmed cell death in cancer cell lines that express functional EGFRs. Furthermore, a potentiation in the growth inhibitory effect on cancer cells was observed following treatment with these EGFR antisense MBOs in combination with various known cytotoxic drugs currently used in the medical treatment of human epithelial malignancies. These and other determinations have been exploited to provide the present invention, which includes synthetic oligonucleotides complementary to EGFR nucleic acid, and methods of their use.

More specifically, in one aspect, the invention provides synthetic oligonucleotides which are complementary to a region of EGFR mRNA selected from the group consisting of locations 245-1117, 2407-3201, 3786-4102, and 4574-4633. In some embodiments, the oligonucleotides of the invention are complementary to a region of EGFR mRNA selected from the group consisting of locations 2407-2476, 4040-4102, and 4574-4633.

In some embodiments, the oligonucleotides of the invention have about 12-30 nucleotides. In preferred embodiments, the oliognucleotides of the invention have about 15 to about 25 nucleotides. In a most preferred embodiment, the oligonucleotide is about 20 nucleotides in length.

In preferred embodiments, the oligonucleotides of the invention comprise at least one modified internucleotide linkage. In a certain embodiment, that internucleotide linkage is a phosphorothioate or phosphorodithioate internucleotide linkage.

In preferred embodiments, the oligonucleotides of the invention comprise at least one 2'-modified ribonucleotide. In some embodiments, the oligonucleotides comprise at least one modified internucleotide linkage and at least one 2'-modified ribonucleotide. In certain embodiments, the oligonucleotide comprises at least three 2'-modified ribonucleotides, or at least four 2'-modified ribonucleotides. In certain embodiments, the 2'-modified ribonucleotide is a 2'-alkyl ribonucleotide. In certain embodiments, the oligonucleotide comprises at least three contiguous deoxyribonucleotides or deoxyribonucleotide phosphorothioates. In certain embodiments, the oligonucleotide comprises at least four contiguous deoxyribonucleotides or deoxyribonucleoside phosphorothioates.

In particular embodiments, the oligonucleotides of the invention comprise a nucleotide sequence selected from the group consisting of SEQ ID NOS: 1, 2, 3, 4, 5, 6, 7, 8, 9, 10, 11, 12, 13, 14, 15, 16, 17, 18, 19, 20, 21, and 22.

In another aspect, the invention also provides a method of inhibiting the synthesis of EGFR in a cell that expresses functional EGFR, comprising contacting the cell with an oligonucleotide of the invention, as described above.

In still another aspect, the invention provides a method of inhibiting the growth of a neoplastic cell expressing a functional EGFR, comprising contacting the cell with an oligonucleotide of the invention, as described above. In some embodiments, the cancer cell is a colon cancer cell, a breast cancer cell, or an ovarian cancer cell.

In yet another aspect, the invention provides a method of enhancing apoptosis in a cancer cell expressing a functional EGFR, comprising contacting the cell with an oligonucleotide of the invention, as described above.

In still another aspect, the invention provides a method of potentiating the growth inhibitory effect of a cytotoxin on a cancer cell, comprising contacting the cancer cell with an oligonucleotide of the invention, as described above, as well as the cytotoxin. In particular embodiments, the cytotoxin is selected from the group consisting of cisplatin, doxorubicin, paclitaxel, topotecan, camptosar, and taxotere. In some embodiments, the cancer cell is a colon, breast or ovarian cancer cell.

DESCRIPTION OF THE DRAWINGS

FIG. 3A is a representation of a Western blot showing p27 expression in GEO cancer cells treated for three days with a scramble sequence oligonucleotide (0.5 µM, lane 1); AS23 oligonucleotide (0.1 µM, lane 2); AS23 oligonucleotide (0.5 µM, lane 3); MAb C225 (1 µg/ml, lane 4); or MAb C225 (5 µg/ml, lane 5). Equal amounts (50 µg/lane) of protein extracts were resolved by a 12% SDS-PAGE and probed with an anti-human p27 MAb. Immunoreactive proteins were visualized by enhanced chemiluminescence.

FIG. 3B is a representation of a Western blot showing p27 expression in ZR-75-1 cancer cells treated for three days with a scramble sequence oligonucleotide (0.5 µM, lane 1); AS23 oligonucleotide (0.1 µM, lane 2); AS23 oligonucleotide (0.5 µM, lane 3); MAb C225 (1 µg/ml, lane 4); or MAb C225 (5 µg/ml, lane 5). Equal amounts (50 µg/lane) of protein extracts were resolved by a 12% SDS-PAGE and probed with an anti-human p27 MAb. Immunoreactive proteins were visualized by enhanced chemiluminescence.

FIG. 5A is a graphic representation showing the growth inhibitory effects of AS23 (0.01 µM, 0.05 nM, 0.1 µM) in combination with cisplatin on the growth of CEO cells in soft agar. Cells were treated with the indicated concentrations of cytotoxic drug on day 1, followed by the indicated concentrations of EGFR-AS oligonucleotide on each day from day 2 to day 4. Colonies were counted after 10 to 14 days. Data represent the average (±standard deviation) of three different experiments, each performed in triplicate.

FIG. 5B is a graphic representation showing the growth inhibitory effects of AS23 (0.01 µM, 0.05 µM, 0.1 µM) in combination with doxorubicin on the growth of GEO cells in soft agar. Cells were treated with the indicated concentrations of cytotoxic drug on day 1, followed by the indicated concentrations of EGFR-AS oligonucleotide on each day from day 2 to day 4. Colonies were counted after 10 to 14 days. Data represent the average (±standard deviation) of three different experiments, each performed in triplicate.

FIG. 5C is a graphic representation showing the growth inhibitory effects of AS23 (0.01 µM, 0.05 µM, 0.1 µM) in combination with paclitaxel on the growth of GEO cells in soft agar. Cells were treated with the indicated concentrations of cytotoxic drug on day 1, followed by the indicated concentrations of EGFR-AS oligonucleotide on each day from day 2 to day 4. Colonies were counted after 10 to 14 days. Data represent the average (±standard deviation) of three different experiments, each performed in triplicate.

FIG. 5D is a graphic representation showing the growth inhibitory effects of AS23 (0.01 µM, 0.05 µM, 0.1 µM) in combination with topotecan on the growth of GEO cells in soft agar. Cells were treated with the indicated concentrations of cytotoxic drug on day 1, followed by the indicated concentrations of EGFR-AS oligonucleotide on each day from day 2 to day 4. Colonies were counted after 10 to 14 days. Data represent the average (±standard deviation) of three different experiments, each performed in triplicate.

DETAILED DESCRIPTION OF THE INVENTION

Figure 1A:
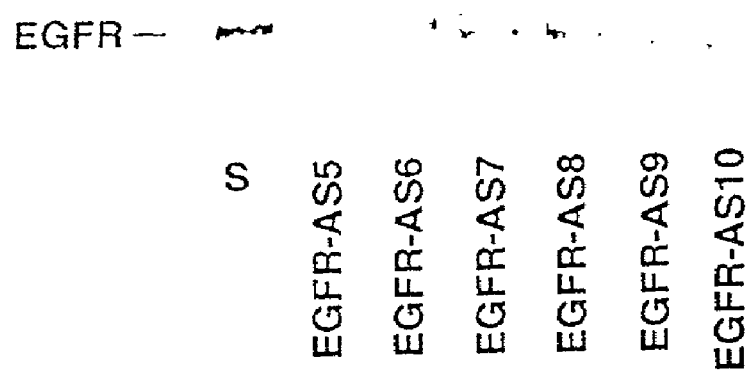
FIG. 1A is a representation of a Western blot showing EGFR expression in GEO cancer cells following treatment with EGFR antisense oligonucleotides. GEO cells were treated for three days with 0.5 µM of the indicated oligonucleotides (AS 5, 6, 7, 8, 9, 10), 0.5 µM, or with 0.5 µM scramble sequence oligonucleotides. Equal amounts (50 µg/lane) of protein extracts were resolved by a 7.5% SDS-PAGE and probed with an anti-human EGFR monoclonal antibody. Immunoreactive proteins were visualized by enhanced chemiluminescence.

The published patent and scientific literature referred to herein establishes knowledge that is available to those with skill in the art. The issued U.S. patents, allowed applications, published foreign patent applications, and references, including GenBank database sequences, that are cited herein are hereby incorporated by reference to the same extent as if each was specifically and individually indicated to be incorporated by reference. Any inconsistency between these publications and the present disclosure shall be resolved in favor of the present disclosure.

This invention relates to the fields of cell biology, medicine and cancer. More specifically, this invention is related to the control of cell proliferation through antisense technology.

It has been discovered that oligonucleotides directed to EGFR-specific mRNA reduces EGFR expression and inhibits cancer cell growth in vitro. In addition, it has also been determined that oligonucleotides modified as hybrid DNA/RNA mixed backbone oligonucleotides (MBOs) specifically target EGFR mRNA sequences and block EGFR synthesis, inhibit cell growth, and enhance apoptosis, or programmed cell death in cancer cell lines that express functional EGFRs. Furthermore, a potentiation in the growth inhibitory effect on cancer cells was observed following treatment with these EGFR antisense MBOs in combination with various known cytotoxic drugs currently used in the medical treatment of human epithelial malignancies. These and other determinations have been exploited to provide the present invention, which includes synthetic oligonucleotides complementary to EGFR nucleic acid, and methods of their use.

For purposes of the invention, the term "oligonucleotide" includes polymers of two or more deoxyribonucleosides, ribonucleosides, or any combination thereof. Preferably, such oligonucleotides have from about 6 to about 50 nucleoside residues, more preferably from about 12 to about 30 nucleoside residues, and most preferable, from about 15 to about 25 nucleoside residues. The nucleoside residues may be coupled to each other by any of the numerous known internucleoside linkages. Such internucleoside linkages include, without limitation, phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate, and sulfone internucleotide linkages. These internucleoside linkages preferably are phosphotriester, phosphorothioate, or phosphoramidate linkages, or combinations thereof. Preferably, oligonucleotides of the invention comprise at least one phosphorothioate or phosphorodithioate internucleotide linkages.

The term "oligonucleotide" also encompasses such polymers as PNA and LNA, and may also include nucleic acid molecules containing 2'-O-substituted ribonucleotides. For purposes of the invention, the term "2'-O-substituted" means substitution of the 2' position of the pentose moiety with an —O-lower alkyl group containing 1-6 saturated or unsaturated carbon atoms, or with an —O-aryl or allyl group having 2-6 carbon atoms, wherein such alkyl, aryl, or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group. The term "alkyl," as employed herein, refers to straight and branched chain aliphatic groups having from 1 to 12 carbon atoms, preferably 1-8 carbon atoms, and more preferably 1-6 carbon atoms, which may be optionally substituted with one, two or three substituents. Unless otherwise apparent from context, the term "alkyl" is meant to include saturated, unsaturated, and partially unsaturated aliphatic groups. When unsaturated groups are particularly intended, the terms "alkenyl" or "alkynyl" will be used. When only saturated groups are intended, the term "saturated alkyl" will be used. Preferred saturated alkyl groups include, without limitation, methyl, ethyl, propyl, isopropyl, butyl, isobutyl, sec-butyl, tert-butyl, pentyl, and hexyl.

Also encompassed by the term "oligonucleotide" are polymers having chemically modified bases or sugars and/or having additional substituents including, without limitation, lipophillic groups, intercalating agents, diamines, and adamantane.

The oligonucleotides of the invention are complementary to nucleic acids encoding EGFR. For purposes of the invention, the term "complementary" means having the ability to hybridize to a genomic region, a gene, or an RNA transcript thereof, under physiological conditions. Such hybridization is ordinarily the result of base-specific hydrogen bonding between complementary strands, preferably to form Watson-Crick or Hoogsteen base pairs, although other modes of hydrogen bonding, as well as base stacking, can lead to hybridization. As a practical matter, such hybridization can be inferred from the observation of specific gene expression inhibition, which may be at the level of transcription or translation (or both). Useful oligonucleotides include chimeric oligonucleotides and hybrid oligonucleotides.

For purposes of the invention, a "chimeric oligonucleotide" refers to an oligonucleotide having more than one type of internucleoside linkage. One preferred embodiment of such a chimeric oligonucleotide is an oligonucleotide comprising internucleoside linkages, phosphorothioate, phosphorodithioate and phosphodiester, preferably comprising from about 2 to about 12 nucleotides. Some useful oligonucleotides of the invention have an alkylphosphonate-linked region and an alkylphosphonothioate region (see e.g., U.S. Pat. Nos. 5,635,377 and 5,366,878). Preferably, useful chimeric oligonucleotides contain at least one, or more preferably, at least three or four consecutive internucleoside linkages that are phosphodiester or phosphorothioate linkages, or combinations thereof. Inverted chimeric oligonucleotides are also contemplated, as described in U.S. Pat. Nos. 5,652,356, 5,973,136, and 5,773,601.

For purposes of the invention, a "hybrid oligonucleotide" refers to an oligonucleotide having more than one type of nucleoside. One preferred embodiment of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide contains at least three consecutive deoxyribonucleosides and contains ribonucleosides, 2'-O-substituted ribonucleosides, or combinations thereof (see e.g., Metelev and Agrawal, U.S. Pat. Nos. 5,652,355 and 5,652,356). Inverted hybrid oligonucleotides are also contemplated as described in U.S. Pat. No. 5,652,356.

Some of the preferred oligonucleotides of the invention are mixed backbone oligonucleotides (MBOs) which contain centrally-modified or end-modified nucleosides with appropriately placed segments of modified internucleotide linkages, such as phosphorothioates, methylphosphonates, phosphodiesters, and segments of modified oligodeoxy- or oligoribo-nucleotides (Agrawal (1997) *Proc. Natl. Acad. Sci. (USA)* 94: 2620-2625; Agrawal (1999) *Biochem. Biophys. Acta* 1489:53-67).

As mentioned above, the oligonucleotides according to the invention are complementary to any region of RNA, DNA, cDNA or double-stranded DNA, and preferably to mRNA, that encodes at least a portion of EGFR. The sequence of EGFR mRNA is known (GenBank accession number M34309). Oligonucleotides of the invention were designed based on the selection criteria described in Agrawal and Kandimalla (2000) *Molecular Medicine Today* 6:72-81.

The exact nucleotide sequence and chemical structure of an antisense oligonucleotide utilized in the invention can be varied, so long as the oligonucleotide retains its ability to modulate expression of the target EGFR sequence. This is readily determined by testing whether the particular antisense oligonucleotide is active by quantitating the amount of EGFR mRNA or quantitating the amount of EGFR present in cancer cell cultures known to be effected by known EGFR-specific oligonucleotides. Also, the ability of an oligonucleotide to inhibit cancer cell growth in an in vitro or in vivo cell growth assay, all of which are described in detail in this specification can also be tested. The term "inhibit expression" and similar terms used herein are intended to encompass any one or more of these parameters.

Twenty-two nonlimiting examples of oligonucleotides directed to different regions of EGFR mRNA are shown in TABLE 1 below and are set forth in the Sequence Listing as SEQ ID NOS: 1-22 and 25-28.

TABLE 1

| Oligo | SEQ ID NO: | Complementary to EGFR mRNA location | Antisense sequence (5' to 3') |
|---|---|---|---|
| AS1 | 1 | 245-264 | ACACTGCCTGAGAGTTGCCC |
| AS2 | 2 | 341-360 | CCATCACCACCTCACACCTC |
| AS3 | 3 | 784-803 | GGTCTTGGTCAATGTCTGGC |
| AS4 | 4 | 998-1117 | TCTACTTCCATCTTGTCAGG |
| AS5 | 5 | 2428-2447 | GTCCACTCTTGTCCTCAATG |
| AS6 | 6 | 2996-3015 | TCCAACACTTGACCATCACC |
| AS7 | 7 | 3182-3201 | CTGGCTCCAGCTCTACTTCC |
| AS8 | 8 | 3784-3803 | TGGACTGTGCCTTCTCCTCC |
| AS9 | 9 | 4041-4060 | GCTCTCATCTCTTCATACCC |
| AS10 | 10 | 4575-4594 | CTCTTCTTGACAGTCTGATG |
| AS11 | 11 | 2407-2416 | ACTTTAATGCAGACTGGAAT |
| AS12 | 12 | 2417-2736 | GTCCTCAATGACTTTAATGC |
| AS13 | 13 | 2444-2463 | AGCTTGAAAACTCTGCCGTC |
| A514 | 14 | 2457-2476 | TATGATCTGTCACAGCTTGA |
| AS15 | 15 | 4040-4059 | TTGCTCAGATGCTGGGCAGG |
| AS16 | 16 | 4050-4069 | CTTCATACCCTTGCTACGAT |
| AS17 | 17 | 4070-4089 | CCCCTGAAAAGCTCTCATCT |
| AS18 | 18 | 4083-4102 | CCTGATGTCCAGGCCCCTGA |
| AS19 | 19 | 4574-4593 | GGAAACAAAGGCACACATAA |
| AS20 | 20 | 4584-4603 | CAGTCTGATGGGAAACAAAG |
| AS21 | 21 | 4604-4623 | CCTCCCTTTCCTCTTCTTGA |
| AS22 | 22 | 4614-4633 | TGCTAGGTTTCCTCCCTTTC |
| AS25 | 25 | 1038-1052 | ACTCCTCCATACTGA |
| AS26 | 26 | 2003-2017 | ACAAGTATCAGAGCC |
| AS27 | 27 | 1572-1596 | GTGGTGGTAGCAGAGCTGCCTATTG |
| AS28 | 28 | 1081-1105 | TGACACAGGATGTTTGATCCACCAC |

Oligonucleotides according to the invention may conveniently be synthesized by any known method, e.g., on a suitable solid support using well-known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon (1993) *Meth. Molec. Biol.* 20:465-496). Additionally, the preparation of these modified oligonucleotides is well known in the art (reviewed in Agrawal (1992) *Trends Biotechnol.* 10:152-158; Agrawal et al. (1995) *Curr. Opin. Biotechnol.* 6:12-19). For example, nucleotides can be covalently linked using art-recognized techniques such as phosphoramidate, H-phosphonate chemistry, or methylphosphoramidate chemistry. Oligomeric phosphorothioate analogs can be prepared using methods well known in the field such as methoxyphosphoramidite (see, e.g., Agrawal et al. (1988) *Proc. Natl. Acad. Sci.* (*USA*) 85:7079-7083) or H-phosphonate (Froehler (1986) *Tetrahedron Lett.* 27:5575-5578) chemistry (see, e.g., U.S. Pat. No. 5,149,798). The synthesis of the phosphorothioate or mixed backbone modified antisense oligonucleotides targeting different regions of the human EGFR mRNA can be performed as described in Agrawal (1997) *Proc. Natl. Acad. Sci.* (*USA*) 94:2620-2625.

Oligonucleotides according to the invention are useful for a variety of purposes, including inhibiting the expression of EGFR genes in cells that normally or usually express EGFR, and potentiating or enhancing the toxic effects of oxidizing agents and cytotoxins on cancer cells. They also can be used as probes of the physiological function of EGFR protein by being used to inhibit the mitogenic activity of EGFR-related proteins in an experimental cell culture or animal system and to evaluate the effect of inhibiting such specific EGFR activity. This is accomplished by administering to a cell or an animal an antisense oligonucleotide that inhibits EGFR protein expression according to the invention, and observing any phenotypic effects. In this use, the oligonucleotides used according to the invention are preferable to traditional "gene knockout" approaches because they are easier to use, and because they can be used to inhibit specific EGFR-related protein activity.

In addition, the cell proliferation inhibiting ability of the EGFR-specific antisense oligonucleotides according to the invention allows the synchronization of a population of a-synchronously growing cells. For example, the antisense oligonucleotides of the invention may be used to arrest a population of non-neoplastic, EGFR-expressing cells grown in vitro in the G1 or G2 phase of the cell cycle. Such synchronization allows, for example, the identification of gene and/or gene products expressed during the G1 or G2 phase of the cell cycle. Such a synchronization of cultured cells may also be useful for testing the efficacy of a new transfection protocol, where transfection efficiency varies and is dependent upon the particular cell cycle phase of the cell to be transfected. Use of the antisense oligonucleotides of the invention allows the synchronization of a population of cells, thereby aiding detection of enhanced transfection efficiency.

The EGFR-specific oligonucleotides of the invention are useful in various methods of the invention, including a method of inhibiting the synthesis of EGFR in a cell that expresses functional EGFR, comprising contacting the cell with an oligonucleotide of the invention, as described above. They are also used to inhibit the growth of a neoplastic or cancer cell expressing a functional EGFR, or to enhance apoptosis, or programmed cell death, in a cancer cell expressing a functional EGFR.

The terms "neoplastic cell" and "cancer cell" are used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastases in vivo and that may recur after attempted removal. The term "tumorigenesis" is used to denote the induction of cell proliferation that leads to the development of a neoplastic or cancerous growth. Such an assessment of cancer cell growth or proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers, and comparing the size of the growth of contacted cells with non-contacted cells. Preferably, the term includes a retardation of cell proliferation that is at least 50% of non-contacted cells. More preferably, the term includes a retardation of cell proliferation that is 100% of non-contacted cells (i.e., the contacted cells do not increase in number or size). Most preferably, the term includes a reduction in the number or size of contacted cells, as compared to non-contacted cells. Thus, an EGFR-specific antisense oligonucleotide of the invention that inhibits cell proliferation in a contacted cell may induce the contacted cell to undergo growth retardation, growth arrest, programmed cell death (i.e., to apoptose), or necrotic cell death. This can be determined as follows.

Antisense oligonucleotides having SEQ ID NOS: 1-10 were designed and evaluated for the ability to inhibit the anchorage-independent growth of human GEO colon cancer cells. Human cancer cells useful for this study are GEO cells. The results are shown in Table 2 below.

TABLE 2

Effects Of Anti-EGFR 20-mer Phosphorothioate Antisense Oligonucleotides On GEG Cancer Cell Growth:

| Oligo | SEQ ID NO: | Complementary to EGFR mRNA location | Antisense sequence (5' to 3') | IC50 (:M) |
|---|---|---|---|---|
| AS1 | 1 | 245-264 | ACACTGCCTGAGAGTTGCCC | 3.5 |
| AS2 | 2 | 341-360 | CCATCACCACCTCACACCTC | 2 |
| AS3 | 3 | 784-803 | GGTCTTGGTCAATGTCTGGC | 1 |
| AS4 | 4 | 998-1117 | TCTACTTCCATCTTGTCAGG | 0.8 |
| AS5 | 5 | 2428-2447 | GTCCACTCTTGTCCTCAATG | 0.7 |
| AS6 | 6 | 2996-3015 | TCCAACACTTGACCATCACC | 0.9 |
| AS7 | 7 | 3182-3201 | CTGGCTCCAGCTCTACTTCC | 1.5 |
| AS8 | 8 | 3784-3803 | TGGACTGTGCCTTCTCCTCC | 0.8 |

TABLE 2-continued

Effects Of Anti-EGFR 20-mer Phosphorothioate Antisense Oligonucleotides On GEG Cancer Cell Growth:

| Oligo | SEQ ID NO: | Complementary to EGFR mRNA location | Antisense sequence (5' to 3') | IC50 (:M) |
|---|---|---|---|---|
| AS9 | 9 | 4041-4060 | GCTCTCATCTCTTCATACCC | 0.6 |
| AS10 | 10 | 4575-4594 | CTCTTCTTGACAGTCTGATG | 0.5 |
| Control | | | Scramble sequence | >25 |

All of the EGFR antisense oligonucleotides listed in Table 2 inhibit the ability of GEO cells to form colonies in soft agar. Similarly, Western blot analysis demonstrated a significant reduction in EGFR expression after treatment with each of these EGFR antisense oligonucleotides (FIG. 1A). The ability of the oligonucleotides to inhibit GEO cell soft agar growth ranged from an $IC_{50}$ of about 0.5 μM (AS10 (SEQ ID NO: 10)) to an $IC_{50}$ of about 3.5 μM (AS1 (SEQ ID NO: 1)).

To further define the regions of the EGFR mRNA that are more efficiently targeted by an antisense approach, three series of four 20-mer phosphorothioate sequences that were contiguous or overlapping the sequences of the three most active antisense oligonucleotides (AS5 (SEQ ID NO: 9), AS9 (SEQ ID NO: 9), and AS10 (SEQ ID NO: 10)) were tested for their ability to inhibit the soft agar growth of GEO cells. The results are shown in Table 3 below.

The $IC_{50}$ determined by treatment with these antisense oligonucleotides varied between 0.1 and 0.7 μM. Based on the nucleotide sequence and on the growth inhibitory activity, two sequences (corresponding to AS14 (SEQ 10 NO: 14) and AS22 (SEQ ID NO: 22)) were modified in their backbone structure as hybrid DNA-RNA 20-mer oligonucleotides (AS23 (SEQ ID NO: 23)) and AS24 (SEQ ID NO: 24)) and further characterized for their biological characteristics. GEO cells were grown as colonies in soft agar and treated with different concentrations of the indicated antisense oligonucleotides. $IC_{50}$ values were obtained from three different experiments, each performed in triplicate. The ability of these MBOs to inhibit human cancer cell growth is shown in Table 4 below.

TABLE 3

Effects Of Anti-EGFR 20-mer Phosphorothioate Antisense Oligonucleotides On GEO Cell Growth:

| Oligo | SEQ ID NO: | Complementary to EGFR mRNA location | Antisense sequence (5' to 3') | IC50 (:M) |
|---|---|---|---|---|
| AS11 | 11 | 2407-2426 | ACTTTAATGCAGACTGGAAT | 0.6 |
| AS12 | 12 | 2417-2736 | GTCCTCAATGACTTTAATGC | 0.7 |
| AS13 | 13 | 2444-2463 | AGCTTGAAAACTCTGCCGTC | 0.5 |
| AS14 | 14 | 2457-2476 | TATGATCTGTCACAGCTTGA | 0.1 |
| AS15 | 15 | 4040-4059 | TTGCTCAGATGCTGGGCAGG | 0.2 |
| AS16 | 16 | 4050-4069 | CTTCATACCCTTGCTACGAT | 0.3 |
| AS17 | 17 | 4070-4089 | CCCCTGAAAAGCTCTCATCT | 0.5 |
| AS18 | 18 | 4083-4102 | CCTGATGTCCAGGCCCCTGA | 0.4 |
| AS19 | 19 | 4574-4593 | GGAAACAAAGGCACACATAA | 0.25 |
| AS20 | 20 | 4584-4603 | CAGTCTGATGGGAAACAAAG | 0.1 |
| AS21 | 21 | 4604-4623 | CCTCCCTTTCCTCTTCTTGA | 0.1 |
| AS22 | 22 | 4614-4633 | TGCTAGGTTTCCTCCCTTTC | 0.1 |

TABLE 4

Effects Of Anti-EGFR 20-mer Antisense MBOs On GEO Cell Growth:

| Oligo | SEQ ID NO: | Complementary to EGFR mRNA location | Antisense sequence (5' to 3') | IC50 (:M) |
|---|---|---|---|---|
| AS23 | 23 | 2457-2476 | UAUGAUCUGUCACAGCUUGA | 0.1 |
| AS24 | 24 | 4614-4633 | UGCUAGGUUUCCUCCCUUUC | 0.25 |
| Control antisense | 29 | | UCGCACCCAUCUCUCUCCUUC | >25 |

In this table, the two oligonucleotides contain phosphorothioate internucleotide linkages, identified by normal face type for the nucleosides flanking each position, and 2'-O-methyl-ribonucleosides modifications, identified by italics face type.

Figure 1B:
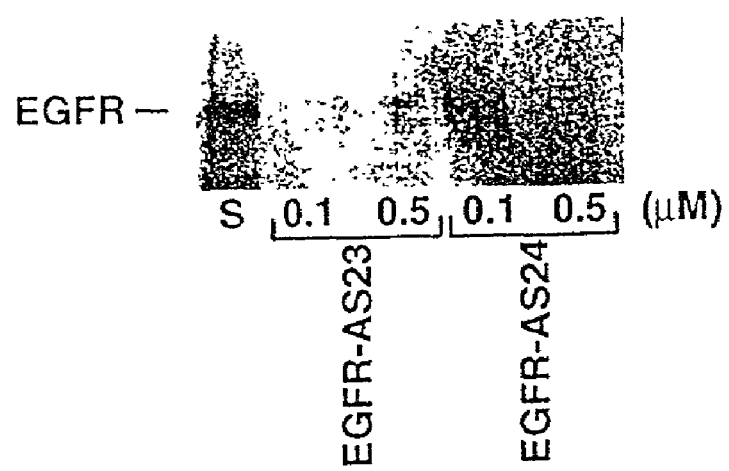
FIG. 1B is a representation of a Western blot showing EGFR expression in CEO cells following treatment with EGFR antisense oligonucleotides. GEO cells were treated for three days with AS23 and AS24 oligonucleotides (0.1 or 0.5 µM), respectively; or with 0.5 µM of scramble sequence oligonucleotides. Equal amounts (50 µg/lane) of protein extracts were resolved by a 7.5% SDS-PAGE and probed with an anti-human EGFR monoclonal antibody. Immunoreactive proteins were visualized by enhanced chemiluminescence.
Figure 1C:
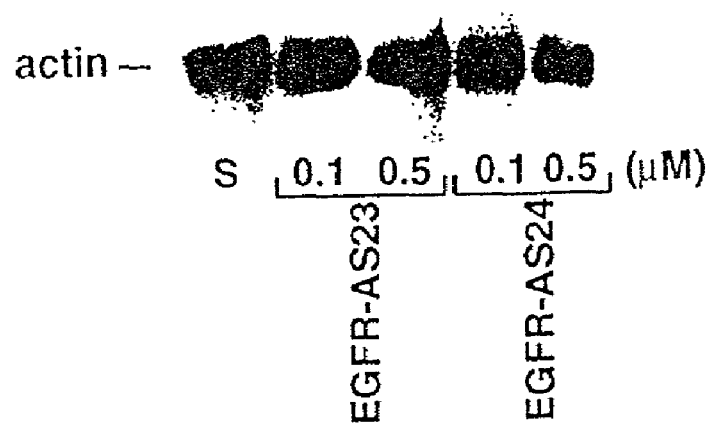
FIG. 1C is a representation of a Western blot showing EGFR expression in GEO cells following treatment with EGFR antisense oligonucleotides. GEO cells were treated for three days with AS23 and AS24 oligonucleotides (0.1 or 0.5 µM), respectively; or with 0.5 µM of a scramble sequence oligonucleotide. Equal amounts (50 µg/lane) of protein extracts were resolved by a 7.5% SDS-PAGE and probed with an anti-human EGFR activin monoclonal antibody. Immunoreactive proteins were visualized by enhanced chemiluminescence.
Figure 2A:
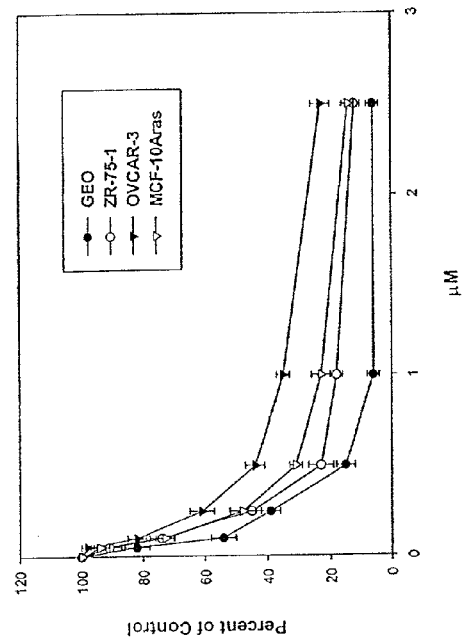
FIG. 2A is a graphic representation of the results of a cell culture assay showing the growth inhibitory effects of AS23 oligonucleotide on human cancer cell lines GEO, ZR-75-1, OVCAR-3, and MCF-10A ras grown in soft agar.
Figure 2B:
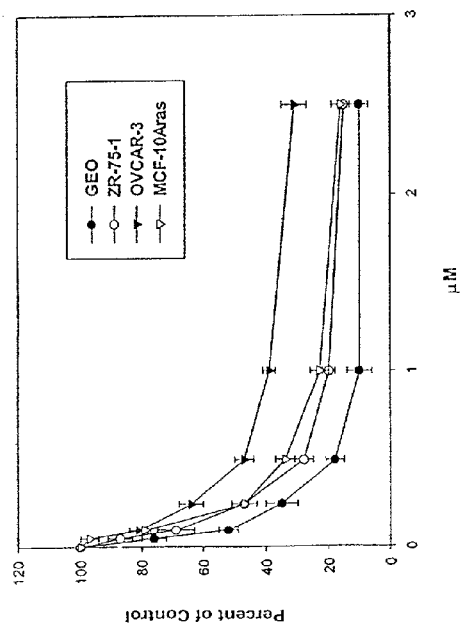
FIG. 2B is a graphic representation of the results of a cell culture assay showing the growth inhibitory effects of AS24 oligonucleotide on human cancer cell lines GEO, ZR-75-1, OVCAR-3, and MCF-10A ras grown in soft agar.
Figure 2C:
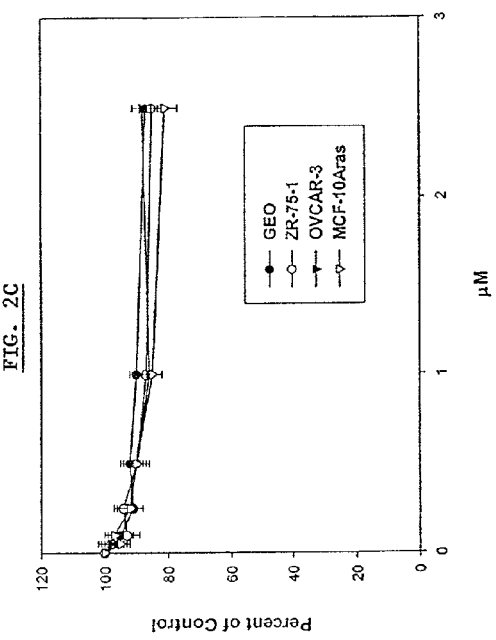
FIG. 2C is a graphic representation of the results of a cell culture assay showing the effect of a control oligonucleotide with a scrambled sequence on human cancer cell lines GEO, ZR-75-1, OVCAR-3, and MCF-10A ras grown in soft agar.

The effect of AS23 and AS24 oligonucleotide treatment on the growth of several cancer cell lines (GEO colon cancer, ZR-75-1, MCF-10A Ha-ras breast cancer, and OVCAR-3 ovarian cancer) in soft agar was then evaluated. As shown in FIGS. 2A and 2B, treatment with both EGFR antisense MBOs demonstrated a dose-dependent inhibition of colony formation in soft agar with an $IC_{50}$ ranging from between 0.1 μM and 0.5 μM in all cancer cell lines tested. In contrast, little or no growth inhibition was observed after treatment with a control, scramble sequence oligonucleotide (FIG. 2C). As shown in FIG. 1B, an almost complete inhibition in EGFR protein expression was detected in GEO cell treated for three days with AS23 or with AS24 at 0.1 μM or 0.5 μM, as compared to scramble oligonucleotide-treated cells.

Treatment with agents that selectively inhibit the EGFR, such as anti-EGFR blocking MAbs, has a cytostatic effect, with cell cycle arrest in the $G_1$ phase and inhibition of cyclin-dependent kinase (CDK)-2 activity that is mainly due to a concomitant increase in the expression of the CDK-inhibitor p27 (Mendelsohn, 1997, supra). The ability of EGFR antisense treatment to induce p27 was therefore examined. As shown in FIG. 3, AS23 treatment of both GEO and ZR-75-1 cancer cells demonstrated a dose-dependent increase in p27 expression.

Figure 4A:
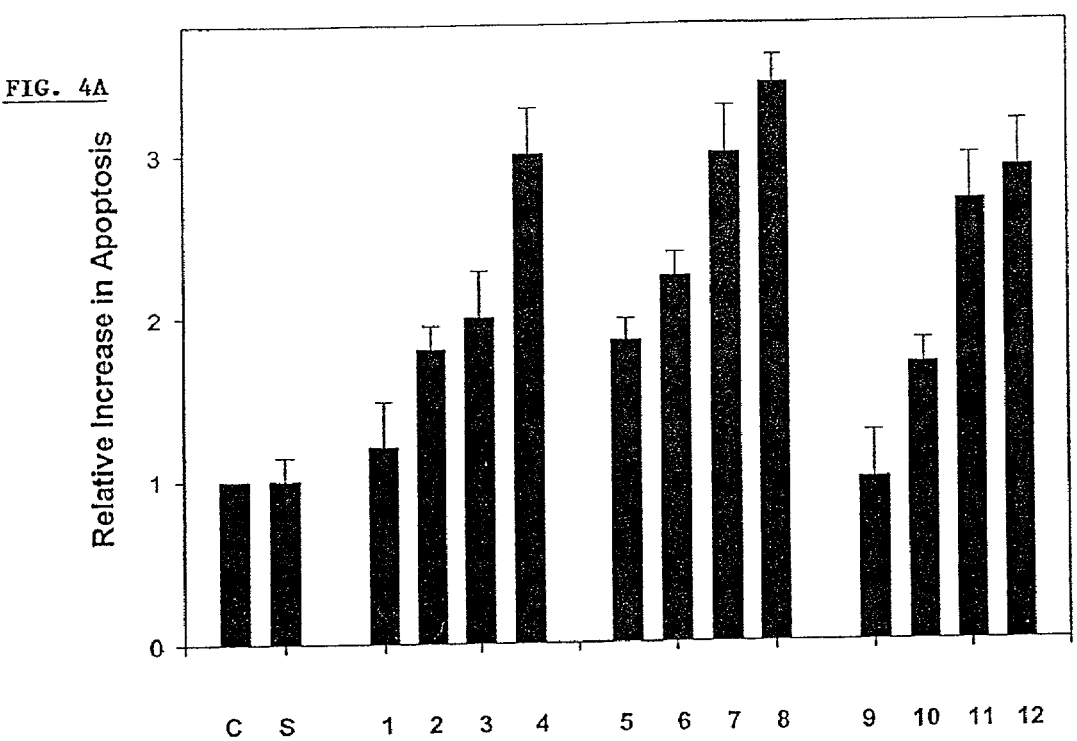
FIG. 4A is a bar graph showing the dose-dependent induction of programmed cell death by treatment of human GEO cancer cells with AS23 and AS24 oligonucleotides. GEO cells were treated each day for 3 days with the following doses of antisense oligonucleotides or monoclonal antibodies: 0.1 µM AS23 (bar 1); 0.5 µM AS23 (bar 2); 1 µM AS23 (bar 3); 2.5 µM AS23 (bar 4); 0.1 µM AS24 (bar 5); 0.5 µM AS24 (bar 6); 1 µM AS24 (bar 7); 2.5 µM AS24 (bar 8), 0.25 µg/ml MAb C225 (bar 9); 0.5 µg/ml MAb C225 (bar 10); 1 µg/ml MAb C225 (bar 11); 5 µg/ml. MAb C225 (bar 12), C, untreated control, S, cells treated with 2.5 µM scramble sequence oligonucleotide. Analysis of apoptosis was performed 4 days after the beginning of treatment. Data represent the average (±standard deviation) of quadruplicate determinations.
Figure 4B:
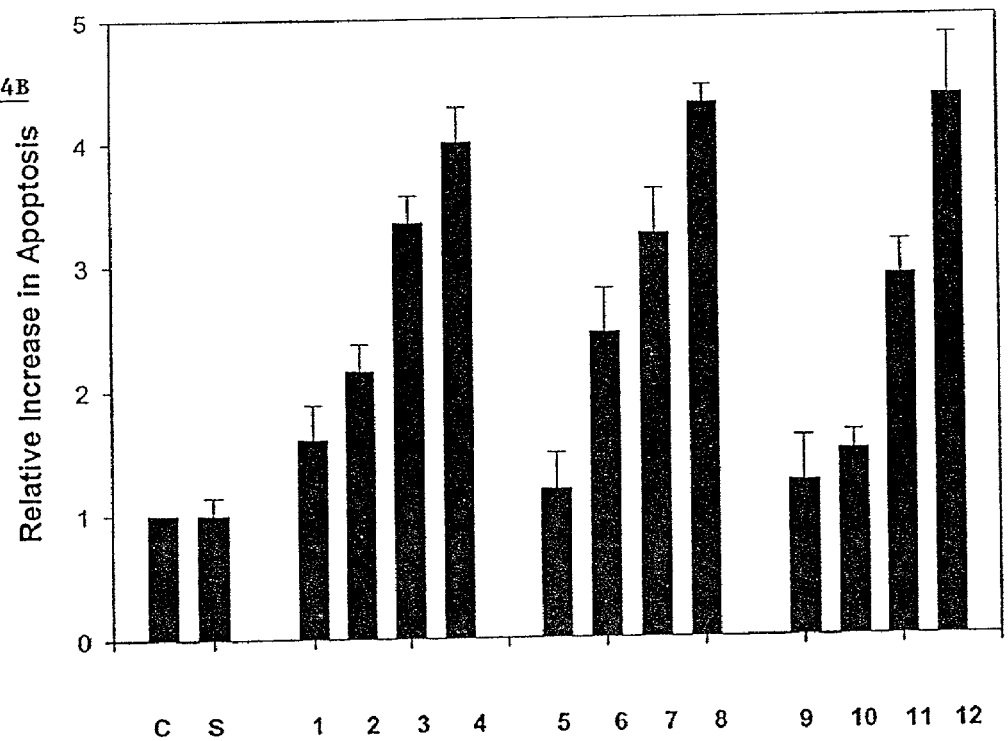
FIG. 4B is a bar graph showing the dose-dependent induction of programmed cell death by treatment with AS23 and AS24 oligonucleotides in human ZR-75-1 cancer cells. GEO cells were treated each day for 3 days with the following doses of antisense oligonucleotides or monoclonal antibodies: 0.1 µM AS23, (bar 1); 0.5 µM AS23 (bar 2); 1 µM AS23 (bar 3); 2.5 µM AS23 (bar 4); 0.1 µM AS24 (bar 5); 0.5 µM AS24 (bar 6); 1 µM AS24 (bar 7); 2.5 µM AS24 (bar 8), 0.25 µg/ml MAb C225 (bar 9); 0.5 µg/ml MAb C225 (bar 10); 1 µg/ml MAb C225 (bar 11); 5 µg/ml. MAb C225 (bar 12), C, untreated control. S, cells treated with the scramble sequence oligonucleotide, 2.5 µM. Analysis of apoptosis was performed 4 days after the beginning of treatment. Data represent the average (±standard deviation) of quadruplicate determinations.
Figure 6B:
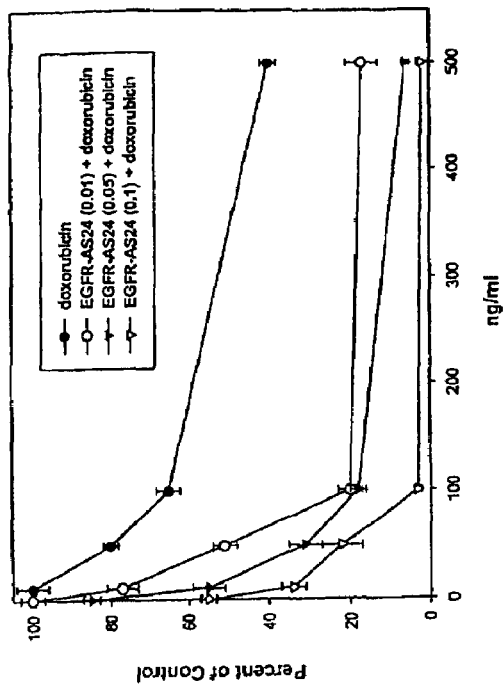
FIG. 6B is a graphic representation showing the growth inhibitory effects of AS24 (0.01 µM, 0.05 µM, 0.1 µM) in combination with doxorubicin on the growth of GEO cells in soft agar. Cells were treated with the indicated concentrations of cytotoxic drug on day 1, followed by the indicated concentrations of AS oligonucleotide on each day from day 2 to day 4. Colonies were counted after 10 to 14 days. Data represent the average (±standard deviation) of three different experiments, each performed in triplicate.
Figure 6D:
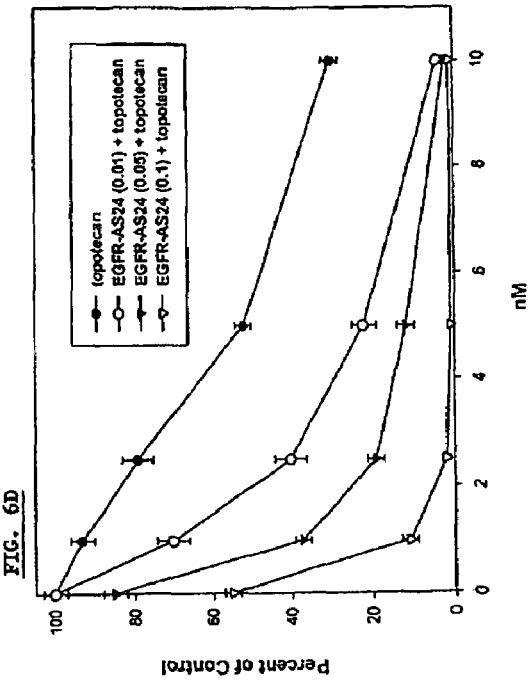
FIG. 6D is a graphic representation showing the growth inhibitory effects of AS24 (0.01 µM, 0.05 µM, 0.1 µM) in combination with topotecan on the growth of GEO cells in soft agar. Cells were treated with the indicated concentrations of cytotoxic drug on day 1, followed by the indicated concentrations of AS oligonucleotide on each day from day 2 to day 4. Colonies were counted after 10 to 14 days. Data represent the average (±standard deviation) of three different experiments, each performed in triplicate.
Figure 6A:
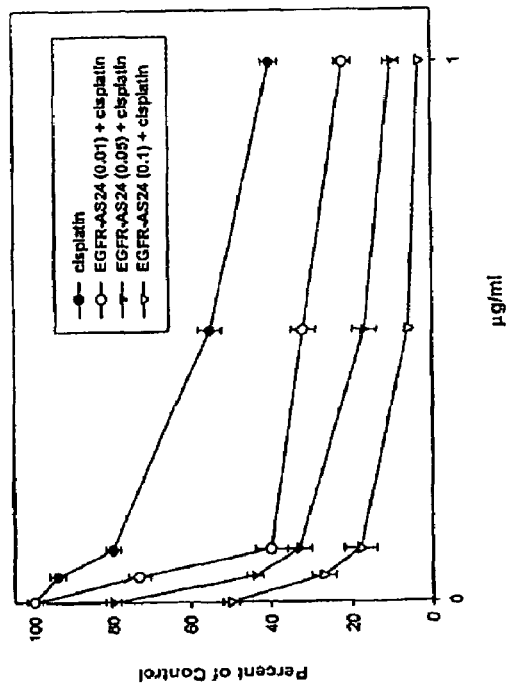
FIG. 6A is a graphic representation showing the growth inhibitory effects of AS24 (0.01 µM, 0.05 µM, 0.1 µM) in combination with cisplatin on the growth of GEO cells in soft agar. Cells were treated with the indicated concentrations of cytotoxic drug on day 1, followed by the indicated concentrations of AS oligonucleotide on each day from day 2 to day 4. Colonies were counted after 10 to 14 days. Data represent the average (±standard deviation) of three different experiments, each performed in triplicate.
Figure 6C:
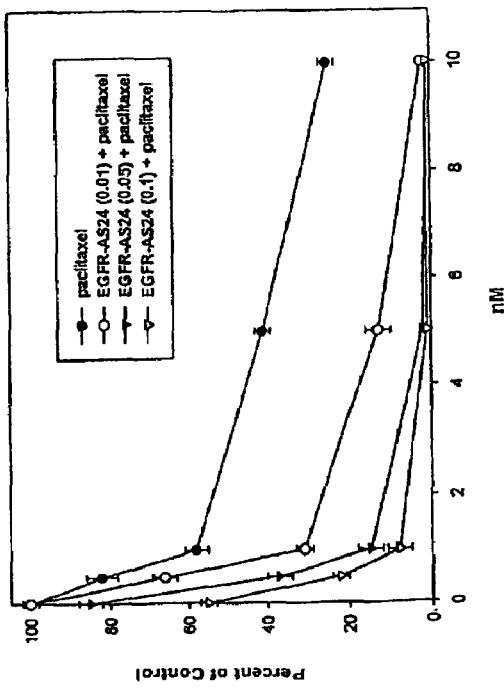
FIG. 6C is a graphic representation showing the growth inhibitory effects of AS24 (0.01 µM, 0.05 µM, 0.1 µM) in combination with paclitaxel on the growth of GEO cells in soft agar. Cells were treated with the indicated concentrations of cytotoxic drug on day 1, followed by the indicated concentrations of AS oligonucleotide on each day from day 2 to day 4. Colonies were counted after 10 to 14 days. Data represent the average (±standard deviation) of three different experiments, each performed in triplicate.

The ability of EGFR antisense treatment to induce programmed cell death was also examined. As illustrated in FIG. 4, AS23 or AS24 treatment induced a dose-dependent increase in apoptosis in GEO and ZR-75-1 cancer cells as compared to control or to scramble oligonucleotide-treated cells, with a maximum 2 to 3-fold increase of between 1 μM and 2.5 μM. This effect was similar to that observed after treatment with MAb C225.

The invention also provides a method of potentiating the growth inhibitory effect of a cytotoxin on a cancer cell. In this method, the cell is contacted with an oligonucleotide of the invention, as well as the cytotoxin. For example, the growth inhibitory effects of AS23 and AS24 on cancer cells were examined in combination with four different cytotoxins: cisplatin, doxorubicin, paclitaxel, and topotecan. The results are shown in FIGS. 5 and 6. A supra-additive growth inhibitory effect (using GEO cells growing on soft agar) was observed with all doses of both EGFR antisense MBOs and each of the four cytotoxic drugs tested. When lower doses of these agents were used, the antiproliferative effect was clearly cooperative. For example, treatment of GEO cells with 0.25 μg/ml cisplatin, or with 0.05 μM AS23 MBO resulted in approximately 20% growth inhibition, whereas the combined treatment of cytotoxin and antisense oligonucleotide caused a 70% inhibition of colony formation in soft agar (FIG. 5A). The cooperativity quotient of this treatment, defined as the ratio between the actual growth inhibition obtained with cisplatin followed by AS23 MBO and the sum of the growth inhibition achieved by each agent, was approximately 1.8.

Accordingly, the synthetic EGFR-specific oligonucleotides of the invention, when in the form of a therapeutic formulation, are also useful in treating diseases, disorders, and conditions associated with cancer. In such methods, a therapeutic amount of a synthetic oligonucleotide of the invention and effective in inhibiting the expression of an EGFR nucleic acid, in some instances with another antitumor agent, are administered to a cell. This cell may be part of a cell culture, a tissue culture, or may be part or the whole body of an animal such as a human or other mammal.

If the cells to be treated by the methods of the invention are in an animal, the oligonucleotides of the invention (and any additional anticancer agents, if part of the therapeutic methods) are administered by conventional procedures as therapeutic compositions in pharmaceutically acceptable carriers. For example, cisplatin and its analogs, as well as other platinum compounds and cytotoxins can be administered to cancer patients as described by Slapak et al. in Harrison's Principles of Internal Medicine, 14th Edition, McGraw-Hill, N.Y. (1998) Chapter 86.

The characteristics of the carrier will depend on the route of administration, as described below. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of EGFR gene or mRNA expression or which will reduce cancer cell proliferation. For example, combinations of synthetic oligonucleotides, each of which is directed to different regions of an EGFR nucleic acid may be used in the pharmaceutical compositions of the invention. The pharmaceutical composition of the invention may further contain nucleotide analogs such as azidothymidine, dideoxycytidine, dideosyinosine, and the like. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-EGFR gene or gene product factor and/or agent to minimize side effects of the anti-EGFR gene factor and/or agent.

The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is conventional in the art, as disclosed, for example, in U.S. Pat. Nos. 4,235,871, 4,501,728, 4,837,028, and 4,737,323. The pharmaceutical composition of the invention may further include compounds such as cyclodextrins and the like which enhance delivery of oligonucleotides into cells, as described by Zhao et al. *Antisense Research & Development* 5:185-192 (1995), or slow release polymers.

As used herein, the term "therapeutically effective amount" means the total amount of each active component of the pharmaceutical composition or method that is sufficient to show a meaningful patient benefit, i.e., reducing the size of a tumor or inhibiting its growth or inhibiting the proliferation rate of cancer cells. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "therapeutically effective amount" and "therapeutically effective period of time" are used to denote known treatments at dosages and for periods of time effective to reduce neoplastic cell growth.

In practicing the method of treatment or use of the present invention, a therapeutically effective amount of one, two, or more of the synthetic oligonucleotides of the invention is administered to a subject afflicted with a disease or disorder related to cancer. The synthetic oligonucleotide of the invention may be administered in accordance with the method of the invention either alone or in combination with various anticancer agents such as, but not limited to, oxidizing agents or cytotoxins, and/or other known therapies for cancer. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

Administration of the synthetic oligonucleotide of the invention used in the pharmaceutical composition or to practice the method of the present invention can be carried out in a variety of conventional ways, such as intraocular administration, oral ingestion, inhalation, or cutaneous, subcutaneous, intramuscular, or intravenous injection. Administration may be bolus, intermittent, or continuous, depending on the condition and response, as determined by those with skill in the art. In some preferred embodiments of the methods of the invention described above, the oligonucleotide is administered locally (e.g., intraocularly or interlesionally) and/or systemically. The term "local administration" refers to delivery to a defined area or region of the body, while the term "systemic administration" is meant to encompass delivery to the whole organism by oral ingestion, or by intramuscular, intravenous, subcutaneous, or intraperitoneal injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, subcutaneous, intramuscular, intraocular, or intraperitoneal injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, subcutaneous, intramuscular, intraperitoneal, or intraocular injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicles as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patient has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the various pharmaceutical compositions used to practice the method of the present invention should contain about 10 µg to about 20 mg of synthetic oligonucleotide per kg body or organ weight.

The duration of intravenous therapy using the pharmaceutical composition of the present invention will vary, depending on the severity of the cell proliferation disorder being treated and the condition and potential idiosyncratic response of each individual patient. Ultimately the attending physician will decide on the appropriate duration of intravenous therapy using the pharmaceutical composition of the present invention.

If oligonucleotides of the invention are administered locoregionally (e.g., intraperitoneal) as opposed to systemically, normal tissue uptake should be reduced. In addition, methods of encapsulating oligonucleotides in liposomes and targeting these liposomes to selected tissues by inserting proteins into the liposome surface is now conventional.

The invention provides various therapeutic methods including a method of potentiating or enhancing the toxic effects of a cytotoxin on a cancer cell. Cancer cells can be or become resistant to chemotherapeutic agents. The oligonucleotides of the invention sensitize such cells to these anticancer treatments. Cancer cells to be treated by the methods of the invention include any cells whose growth is uncontrolled and include, but not limited to, ovarian, breast, and colon carcinoma cells. Cancer cells which are resistant to chemotherapeutic agents respond particularly well to the methods of the invention.

Preferably, the methods of treating cancer or of inhibiting the growth of a cancer cell according to the invention comprise contacting the cell with, or administering to the tissue or individual afflicted with the neoplasm, a first agent comprising a synthetic oligonucleotide complementary to, and capable of down-regulating the expression of, nucleic acid encoding EGFR according to the invention; and administering a second agent comprising a cytotoxic agent. The oligonucleotide and the cytotoxin may be used or administered simultaneously. Sometimes, the cytotoxin is used or administered prior to the use or administration of the oligonucleotide.

In certain preferred embodiments, the cytotoxin is a taxane, platinum-derived agent, a disrupter of the cellular microtubular network, or topoisomerase I- or II-selective drugs. Useful cytotoxins are taxanes including, but not limited to, pacitaxel and docetaxel. Pacitaxel and docetaxel are commercially obtainable from Sigma (St. Louis, Mo.). Useful platinum-denied agents include cisplatin, oxaliplatin, carboplatin, and analogs and derivatives thereof. Cisplatin (CIS-diamminedichloroplatinum) can be commercially obtained, for example, from Bristol-Meters Squibb (Princeton, N.J.), or Sigma (St. Louis, Mo.). Oxaliplatin can be commercially obtained, for example, from Sigma (St. Louis, Mo.). Carboplatin (platinum, diammine [1,1-cyclobutane-dicarboxylato (2-)-0,0']-,(SP-4-2) can be commercially obtained, for example, from Bristol-Myers Squibb (Princeton, N.J.). Useful topoisomerase inhibitors include, but are not limited to, topotecan and camptosar. Topotecan can be commercially obtained, for example, from Smith-Kline Beechman Italia. Camptosar (irinotecan hydrochloride) is commercially obtainable from Pharmacia & Upjohn (Peapack, N.J.). A nonlimiting example of a compound which disrupts the cellular microtubular network is taxotere ((2R,3S)-N-carboxy-3-phenylisoserine, N-tert-butyl ester, 13-ester), which is commercially obtainable from Rhone-Poulenc, Rorer Pharmaceuticals, Inc. (Collegeville, Pa.).

These cytotoxins can be administered to cancer patients as described, for example, in *Harrison's Principles of Internal Medicine* 14th Edition, McGraw-Hill, NY (1998) and in *Physicians Desk Reference* 54th Ed., Medical Economics Co., Montvale, N.J. (2000). For example, paclitaxel is preferably administered in doses of up to 300 mg/m$^2$/dose by intravenous infusion (1 hour to 24 hour duration), given at a frequency of every 21 days or less. Preferably, docetaxel is administered in doses of up to 300 mg/m$^2$/dose by intravenous infusion (1 hour to 24 hour duration), given at a frequency of every 21 days or less. The amount of cytotoxin to be administered to the cells in the methods of the invention can also be determined by performing dose response experiments with cancerous cells that have not been treated with oligonucleotides directed to EGFR genes.

Standard reference works setting forth the general principles of the genetic and molecular biology technology described herein include Ott and Hoh, "Statistical Approaches to Genetic Mapping," *Am. J. Hum. Genet.* 67:289-294 (2000); Zubay G., *Genetics* The Benjamin/Cummings Publishing Co., Inc., Menlo Park, Calif. (1987); Ausubel et al., *Current Protocols in Molecular Biology*, John Wiley & Sons, New York, N.Y. (1999); Sambrook et al., *Molecular Cloning: A Laboratory Manual,* 2d Ed., Cold Spring Harbor Laboratory Press, Plainview, N.Y. (1989); Kaufman et al. (Eds.), *Handbook of Molecular and Cellular Methods in Biology and Medicine*, CRC Press, Boca Raton, La. (1995); and McPherson, Ed., *Directed Mutagenesis: A Practical Approach*, IRL Press, Oxford (1991). Standard reference works setting forth the general principles of immunology and inflammation include Gallin et al., *Inflammation: Basic Principles and Clinical Correlates*, Raven Press, New York (1988); Kuby, J., *Immunology,* 3rd ed., W.H. Freeman, New York (1997); Coligan et al. (Eds.), *Current Protocols in Immunology*, John Wiley & Sons, New York (1991); and Hurley, J. V., *Acute Inflammation,* 2nd ed., Churchill Livingstone, New York (1983).

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLES

1. Synthesis of Antisense Oligonucleotides

Antisense oligonucleotides targeting EGFR mRNA (GenBank accession number M34309) were designed based on the selection criteria described earlier (Agrawal and Kandimalla, *Molecular Medicine Today* (2000) 6:72-81). Synthesis of 20-mer phosphorothioate or mixed backbone modified antisense oligonucleotides targeting different regions of the human EGFR mRNA was performed using standard procedures (see, e.g., Agrawal (1997) *Proc. Natl. Acad. Sci. (USA)* 94:2620-2625). The identity and purity of the oligonucleotides were confirmed by conventional $^{31}$P nuclear magnetic resonance, capillary gel electrophoresis, hybridization melting temperature, $A_{269}$/and MALDI/TOF mass ratio spectral analysis (see, e.g., Agrawal (1997) *Proc. Natl. Acad. Sci. (USA)* 94:2620-2625).

2. Cells

GEO human colon cancer, OVCAR-3 human ovarian cancer, and ZR-75-1 human breast cancer cell lines were obtained from the American Type Culture Collection, Manassas, Va. (OVCAR, ATCC No. HTB-161; ZR-75-1, ATCC No. CRL-1500). MCF-10A Ha-ras cells have been obtained by the cotransfection of human nontransformed MCF-10A cells with an expression plasmid containing the human activated c-Ha-ras protooncogene and an expression plasmid containing the neomycin-resistance gene (Ciardiello et al. (1990) *Cell Growth Differ.* 1:407-420). All these cell lines express functional EGFR, ranging from approximately 20.000 (ZR-75-1) to 40.000 (GEO), 150.000 (OVCAR-3), 250.000 (MCF-10A Ha-ras) EGF binding sites/cell, and secrete high levels of TGFα (Ciardiello et al. (1999) *Clin. Cancer Res.* 5:909-916). GEO, OVCAR-3 and ZR-75-1 cells were maintained in DMEM supplemented with 10% heat-inactivated fetal bovine serum, 20 mM HEPES, pH 7.4, penicillin (100 UI/ml), streptomycin (100 μg/ml) and 4 mM glutamine (ICN, Irvine, UK) in a humidified atmosphere of 95% air and 5% $CO_2$ at 37° C. MCF-10A Ha-ras cells were grown in a 1:1 (v/v) Dulbecco's modified Eagle Medium (DMEM) and Ham's F12 mixture, supplemented with 5% heat inactivated horse serum, 20 mM Hepes, pH 7.4, 4 mM glutamine, 0.5 μg/ml hydrocortisone (Sigma, St. Louis, Mo.), 10 ng/ml EGF, 10 μg/ml insulin (Collaborative Research Products, Bedford, Mass.), 100 U/ml penicillin and 100 μg/ml streptomycin in a humidified atmosphere of 95% air and 5% $CO_2$ at 37° C.

Cells ($10^4$ cells/well) were suspended in 0.5 ml of 0.3% Difco Noble agar (Difco, Detroit, Mich.) supplemented with complete culture medium. This suspension was layered over 0.5 ml of 0.8% agar-medium base layer in 24 multiwell cluster dishes (Becton Dickinson, Lincoln Park, N.J.) and treated on days 1, 2 and 3 with different concentrations of the various EGFR-AS oligonucleotides alone and/or in combination on day 1 with the indicated concentrations of cytotoxic drugs. After 10 to 14 days, cells were stained with nitro blue tetrazolium (Sigma, St. Louis, Mo.) and colonies larger than 0.05 mm were counted.

3. Western Blot Analysis

50 µg total cell lysates from GEO cells, which were treated each day for three days with the indicated concentrations of antisense oligonucleotides, were fractionated through 7.5% or 12% sodium dodecyl sulfate-polyacrylamide gels, transferred to nitrocellulose filters and incubated with an anti-human EGFR mouse MAb or with an anti-human p27 mouse MAb (both antibodies were purchased from Transduction Laboratories, Lexington, Ky.), respectively, followed by horseradish-peroxidase antiserum (Bio-Rad Laboratories, Milano, Italy). Immunoreactive proteins were visualized by enhanced chemiluminescence (Amersham International, England).

4. Apoptosis Assay

The induction of programmed cell death was determined as described by De Luca et al. (Int. J. Cancer (1999) 8:589-594) using the Cell Death Detection ELISA Plus Kit (Boheringher Mannheim, Indianapolis, Ind.). Briefly, $5 \times 10^4$ cells/well were seeded into 6-multiwell cluster dishes. After treatment with different concentrations of oligos (days 0, 1, and 2) and/or the cytotoxic drug (day 2), on day 4 the cells were washed with PBS and 0.5 ml lysis buffer was added. After a 30 minute incubation, the supernatant was recovered and assayed for DNA fragments as recommended by the manufacturer at 405 nm using a Microplate Reader Model 3550-UV (Bio-Rad, Milan, Italy). Each treatment was performed in quadruplicate. Additional plates identically treated were analyzed for cell number with an hemocytometer to normalize the values for cell numbers, and the results are expressed relative as to untreated control samples.

EQUIVALENTS

As will be apparent to those skilled in the art to which the invention pertains, the present invention may be embodied in forms other than those specifically disclosed above without departing from the spirit or essential characteristics of the invention. The particular embodiments of the invention described above are, therefore, to be considered as illustrative and not restrictive. The scope of the invention is as set forth in the appended claims rather than being limited to the examples contained in the foregoing description.

The sequence of EGFR mRNA (SEQ ID NO: 30) (GenBank accession number M34309) is shown in below in Table 5.

TABLE 5

EGFR mRNA

| | | | | | |
|---:|---|---|---|---|---|
| 1 | ctctcacaca | cacacacccc | tccctcccg | tccctccccg | gactccggct ccggctccga |
| 61 | ttgcaatttg | caacctccgc | tgccgtcgcc | gcagcagcca | ccaattcgcc agcggttcag |
| 121 | gtggctcttg | cctcgatgtc | ctagcctagg | ggccccgggg | ccggacttgg ctgggctccc |
| 181 | ttcaccctct | gcggagtcat | gagggcgaac | gacgctctgc | aggtgctggg cttgcttttc |
| 241 | agcctggccc | ggggctccga | ggtgggcaac | tctcaggcag | tgtgtcctgg gactctgaat |
| 301 | ggcctgagtg | tgaccggcga | tgctgagaac | caataccaga | cactgtacaa gctctacgag |
| 361 | aggtgtgagg | tggtgatggg | gaaccttgag | attgtgctca | cgggacacaa tgccgacctc |
| 421 | tccttcctgc | agtggattcg | agaagtgaca | ggctatgtcc | tcgtggccat gaatgaattc |
| 481 | tctactctac | cattgcccaa | cctccgcgtg | gtgcgaggga | cccaggtcta cgatgggaag |
| 541 | tttgccatct | tcgtcatgtt | gaactataac | accaactcca | gccacgctct gcgccagctc |
| 601 | cgcttgactc | agctcaccga | gattctgtca | gggggtgttt | atattgagaa gaacgataag |
| 661 | ctttgtcaca | tggacacaat | tgactggagg | gacatcgtga | gggaccgaga tgctgagata |
| 721 | gtggtgaagg | acaatggcag | aagctgtccc | ccctgtcatg | aggtttgcaa ggggcgatgc |
| 781 | tggggtcctg | gatcagaaga | ctgccagaca | ttgaccaaga | ccatctgtgc tcctcagtgt |
| 841 | aatggtcact | gctttgggcc | caaccccaac | cagtgctgcc | atgatgagtg tgccggggc |
| 901 | tgctcaggcc | ctcaggacac | agactgcttt | gcctgccggc | acttcaatga cagtggagcc |
| 961 | tgtgtacctc | gctgtccaca | gcctcttgtc | tacaacaagc | taactttcca gctggaaccc |
| 1021 | aatccccaca | ccaagtatca | gtatggagga | gtttgtgtag | ccagctgtcc ccataacttt |
| 1081 | gtggtggatc | aaacatcctg | tgtcagggcc | tgtcctcctg | acaagatgga agtagataaa |

TABLE 5-continued

| | EGFR mRNA |
|---|---|
| 1141 | aatgggctca agatgtgtga gccttgtggg ggactatgtc ccaaagcctg tgagggaaca |
| 1201 | ggctctggga gccgcttcca gactgtggac tcgagcaaca ttgatggatt tgtgaactgc |
| 1261 | accaagatcc tgggcaacct ggactttctg atcaccggcc tcaatgaga ccctggcac |
| 1321 | aagatccctg ccctggaccc agagaagctc aatgtcttcc ggacagtacg ggagatcaca |
| 1381 | ggttacctga acatccagtc ctggccgccc cacatgcaca acttcagtgt ttttccaat |
| 1441 | ttgacaacca ttggaggcag aagcctctac aaccggggct tctcattgtt gatcatgaag |
| 1501 | aacttgaatg tcacatctct gggcttccga tccctgaagg aaattagtgc tgggcgtatc |
| 1561 | tatataagtg ccataggca gctctgctac caccactctt tgaactggac caaggtgctt |
| 1621 | cgggggccta cggaagagcg actagacatc aagcataatc ggccgcgcag agactgcgtg |
| 1681 | gcagagggca aagtgtgtga cccactgtgc tcctctgggg gatgctgggg cccaggccct |
| 1741 | ggtcagtgct tgtcctgtcg aaattatagc cgaggagtg tctgtgtgac ccactgcaac |
| 1801 | tttctgaatg gggagcctcg agaatttgcc catgaggccg aatgcttctc ctgccacccg |
| 1861 | gaatgccaac ccatgggggg cactgccaca tgcaatggct cgggctctga tacttgtgct |
| 1921 | caatgtgccc attttcgaga tgggccccac tgtgtgagca gctgccccca tggagtccta |
| 1981 | ggtgccaagg cccaatcta caagtaccca gatgttcaga atgaatgtcg gccctgccat |
| 2041 | gagaactgca cccaggggtg taaaggacca gagcttcaag actgtttagg acaaacactg |
| 2101 | gtgctgatcg gcaaaaccca tctgacaatg ctttgcacag tgatagcagg attggtagtg |
| 2161 | attttcatga tgctgggcgg cacttttctc tactggcgtg ggcgccggat tcagaataaa |
| 2221 | agggctatga gcgatactt ggaacggggt gagagcatag agcctctgga ccccagtgag |
| 2281 | aaggctaaca agtcttggc cagaatcttc aaagagacag agctaaggaa gcttaaagtg |
| 2341 | cttggctcgg tgtctttgg aactgtgcac aaaggagtgt ggatccctga gggtgaatca |
| 2401 | atcaagattc cagtctgcat taaagtcatt gaggacaaga gtggacggca gagttttcaa |
| 2461 | gctgtgacag atcatatgct ggccattggc agcctggacc atgcccacat tgtaaggctg |
| 2521 | ctgggactat gcccagggtc atctctgcag cttgtcactc aatatttgcc tctgggttct |
| 2581 | ctgctggatc atgtgagaca acaccggggg gcactggggc cacagctgct gctcaactgg |
| 2641 | ggagtacaaa ttgccaaggg aatgtactac cttgaggaac atggtatggt gcatagaaac |
| 2701 | ctggctgccc gaaacgtgct actcaagtca cccagtcagg ttcaggtggc agattttggt |
| 2761 | gtggctgacc tgctgcctcc tgatgataag cagctgctat acagtgaggc caagactcca |
| 2821 | attaagtgga tggcccttga gagtatccac tttgggaaat acacacacca gagtgatgtc |
| 2881 | tggagctatg gtgtgacagt ttgggagttg atgaccttcg ggcagagcc ctatgcaggg |
| 2941 | ctacgattgg ctgaagtacc agacctgcta gagaagggg agcggttggc acagcccag |
| 3001 | atctgcacaa ttgatgtcta catggtgatg gtcaagtgtt ggatgattga tgagaacatt |
| 3061 | cgcccaacct ttaaagaact agccaatgag ttcaccagga tggcccgaga cccaccacgg |
| 3121 | tatctggtca taaagagaga gagtgggcct ggaatagccc ctgggccaga gcccatggt |
| 3181 | ctgacaaaca agaagctaga ggaagtagag ctggagccag aactagacct agacctagac |
| 3241 | ttggaagcag aggaggacaa cctggcaacc accacactgg gctccgccct cagcctacca |
| 3301 | gttggaacac ttaatcggcc acgtgggagc cagagccttt taagtccatc atctggatac |
| 3361 | atgcccatga accagggtaa tcttgggggg tcttgccagg agtctgcagt ttctgggagc |
| 3421 | agtgaacggt gccccccgtcc agtctctcta cacccaatgc cacggggatg cctggcatca |

TABLE 5-continued

EGFR mRNA

```
3481  gagtcatcag aggggcatgt aacaggctct gaggctgagc tccaggagaa agtgtcaatg
3541  tgtagaagcc ggagcaggag ccggagccca cggccacgcg gagatagcgc ctaccattcc
3601  cagcgccaca gtctgctgac tcctgttacc ccactctccc cacccgggtt agaggaagag
3661  gatgtcaacg gttatgtcat gccagataca cacctcaaag gtactccctc ctcccgggaa
3721  ggcacccttt cttcagtggg tctcagttct gtcctgggta ctgaagaaga agatgaagat
3781  gaggagtatg aatacatgaa ccggaggaga aggcacagtc cacctcatcc ccctaggcca
3841  agttcccttg aggagctggg ttatgagtac atggatgtgg ggtcagacct cagtgcctct
3901  ctgggcagca cacagagttg cccactccac cctgtaccca tcatgcccac tgcaggcaca
3961  actccagatg aagactatga atatatgaat cggcaacgag atggaggtgg tcctggggt
4021  gattatgcag ccatgggggc ctgcccagca tctgagcaag ggtatgaaga gatgagagct
4081  tttcaggggc ctggacatca ggccccccat gtccattatg cccgcctaaa aactctacgt
4141  agcttagagg ctacagactc tgcctttgat aaccctgatt actggcatag caggcttttc
4201  cccaaggcta atgcccagag aacgtaactc ctgctccctg tggcactcag ggagcattta
4261  atggcagcta gtgcctttag agggtaccgt cttctcccta ttccctctct ctcccaggtc
4321  ccagccccctt ttccccagtc ccagacaatt ccattcaatc tttggaggct tttaaacatt
4381  ttgacacaaa attcttatgg tatgtagcca gctgtgcact tcttctcctt tcccaacccc
4441  aggaaaggtt ttccttatttt tgtgtgcttt cccagtccca ttcctcagct tcttcacagg
4501  cactcctgga gatatgaagg attactctcc atatcccttc ctctcaggct cttgactact
4561  tggaactagg ctcttatgtg tgcctttgtt tcccatcaga ctgtcaagaa gaggaaaggg
4621  aggaaaccta gcagaggaaa gtgtaatttt ggtttatgac tcttaaccccc ctagaaagac
4681  agaagcttaa aatctgtgaa gaaagaggtt aggagtagat attgattact atcataattc
4741  agcacttaac tatgagccag gcatcatact aaacttcacc tacattatct cacttagtcc
4801  tttatcatcc ttaaaacaat tctgtgacat acatattatc tcattttaca caaagggaag
4861  tcgggcatgg tggctcatgc ctgtaatctc agcactttgg gaggctgagg cagaaggatt
4921  acctgaggca aggagtttga gaccagctta gccaacatag taagaccccc atctc
```

---

The invention claimed is:

1. A synthetic antisense oligonucleotide complementary to a nucleic acid encoding epidermal growth factor receptor (EGFR) comprising at least one phosphorothioate internucleotide linkage, the oligonucleotide comprising the nucleotide sequence set forth in the Sequence Listing as SEQ ID NO: 5, 11, 12, 13, 14, or 23.

2. The oligonucleotide of claim 1 wherein the oligonucleotide is 20 nucleotides in length.

3. The oligonucleotide of claim 1, comprising a 2'-modified ribonucleotide.

4. The oligonucleotide of claim 1, comprising at least four 2'-modified ribonucleotides.

5. The oligonucleotide of claim 3, wherein the 2'-modified ribonucleotide is a 2'-alkyl ribonucleotide.

6. A method of inhibiting the synthesis of epidermal growth factor receptor (EGFR) in a cell that expresses functional EGFR, comprising contacting the cell with the oligonucleotide of claim 1.

7. A method of inhibiting the growth of a cancer cell expressing a functional epidermal growth factor receptor (EGFR), comprising contacting the cell with the oligonucleotide of claim 1.

8. The method of claim 7, wherein the cancer cell is a colon, ovarian or breast cancer cell.

9. A method of enhancing apoptosis in a cancer cell expressing a functional epidermal growth factor receptor (EGFR), comprising contacting the cell with the oligonucleotide of claim 1.

10. The method of claim 9, wherein the cancer cell is a colon, ovarian or breast cancer cell.

11. A method of potentiating the growth inhibitory effect of a cytotoxin in a cancer cell, comprising contacting the cell with the oligonucleotide of claim 1 and the cytotoxin.

12. The method of claim 11, herein the cancer cell is a colon, ovarian or breast cancer cell.

13. The method of claim 11, wherein the cytotoxin is selected from the group consisting of cisplatin, doxorubicin, paclitaxel, topotecan, camptosar, and taxotere.

* * * * *